United States Patent [19]

Matthias et al.

[11] Patent Number: 4,917,894

[45] Date of Patent: Apr. 17, 1990

[54] RAPID-ONSET LONG-DURATION ORAL ANESTHETIC COMPOSITION

[75] Inventors: Joseph A. Matthias, Lake Mohawk; Kim L. Bildstein, Chester, both of N.J.

[73] Assignee: Beecham Inc., Clifton, N.J.

[21] Appl. No.: 212,900

[22] Filed: Jun. 29, 1988

[51] Int. Cl.[4] .............................................. A61K 9/68
[52] U.S. Cl. .................................... 424/440; 424/435; 424/464; 424/49; 514/317; 514/901; 514/948
[58] Field of Search ................. 424/440, 49, 435, 464, 424/465; 514/317, 439, 901, 948

[56] References Cited

U.S. PATENT DOCUMENTS

| | | | |
|---|---|---|---|
| 2,771,391 | 11/1956 | Bockstahler | 424/267 |
| 2,868,689 | 1/1959 | Florestano et al. | 167/52 |
| 2,890,151 | 6/1969 | White | 167/58 |
| 2,937,971 | 5/1960 | Shackell | 167/31 |
| 4,139,627 | 2/1979 | Lane et al. | 424/267 |
| 4,312,865 | 1/1982 | Szucs | 424/243 |
| 4,333,941 | 6/1982 | Baratz et al. | 424/267 |
| 4,372,942 | 2/1983 | Cimiluca | 424/16 |
| 4,639,367 | 2/1987 | Mackles | 424/45 |
| 4,808,410 | 2/1989 | Sorrentino et al. | 424/435 |

FOREIGN PATENT DOCUMENTS 2123278 9/1972 France .

Primary Examiner—Thurman K. Page
Attorney, Agent, or Firm—Jacobs & Jacobs

[57] ABSTRACT

An oral anesthetic composition comprising an anesthetically effective amount of a compound of formula (I)

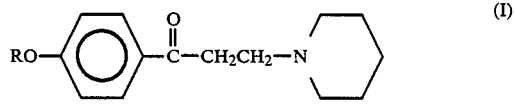

wherein R is alkyl of 2 to 8 carbon atoms or a pharmaceutically acceptable salt thereof and an anesthetically effective amount of a rapid-onset anesthetic selected from the group consisting of benzyl alcohol, phenol, phenolate sodium, hexylresorcinol, menthol, salicyl alcohol and benzocaine in combination with a pharmaceutically acceptable carrier, said carrier being in orally administrable form.

7 Claims, 1 Drawing Sheet

ANESTHETIC EFFECT OF ORAL ANESTHETIC COMPOSITIONS

ANESTHETIC AGENT
○ - PHENOL
□ - DYCLONINE HYDROCHLORIDE
△ - DYCLONINE HYDROCHLORIDE AND PHENOL

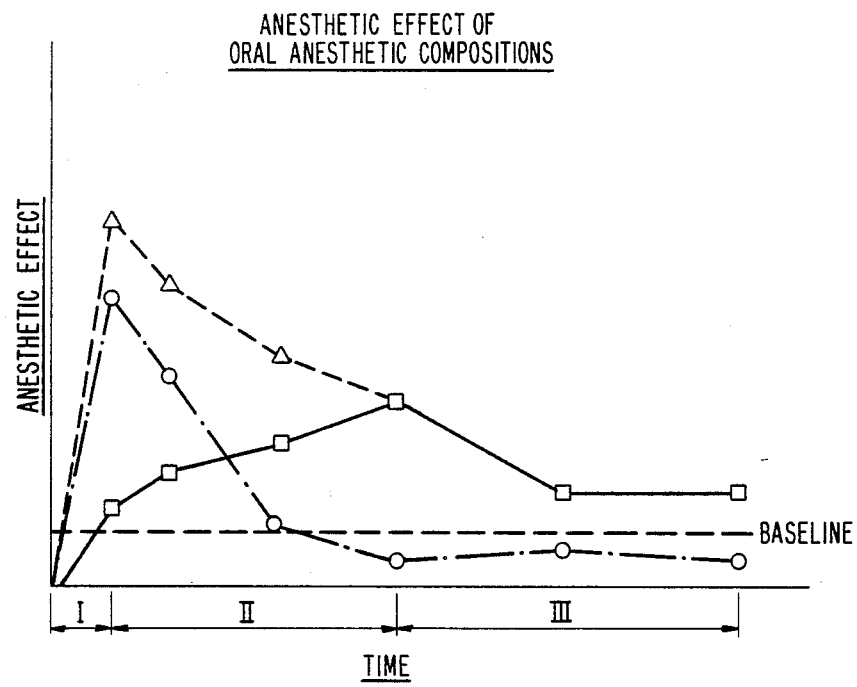

RAPID-ONSET LONG-DURATION ORAL ANESTHETIC COMPOSITION

The present invention relates to over-the-counter ("OTC") oral anesthetic compositions, and more particularly to a novel OTC rapid-onset long-duration anesthetic composition that has been hitherto unavailable.

In the Food and Drug Administration's Tentative Final Monograph, Oral Health Care Drug Products for Overthe-Counter Human Use, eight compounds have been established as both safe and effective (21 CFR |356.10) when used in the dosages and dosage forms established for each ingredient [21 CFR |356.55(d)]. These ingredients and the safe and effective dosages and dosage forms are as follows. In the monograph, the term "solid dosage form" includes all solid forms, such as lozenges and compressed tablets, whereas "dosage forms other than solid" includes all non-solid forms, such as gargles, mouthwashes (oral rinses), sprays, gels and the like.

| Anesthetic | Dosage Forms Other Than Solid (%) | Solid Dosage Forms (mg. per dose) |
|---|---|---|
| Benzocaine | 5–20 | 2–15 |
| Benzyl Alcohol | 0.05–10.00 | 100–500 |
| Dyclonine Hydrochloride | 0.05–0.10 | 1–3 |
| Hexylresorcinol | 0.05–0.10 | 2–4 |
| Menthol | 0.04–2.00 | 2–20 |
| Phenol Preparations* | 0.05–1.50 | 10–50 |
| Salicyl Alcohol | 1–6 | 50–100 |

*Phenol and phenolate sodium

While these anesthetics are all effective, they sharply differ in their action. Thus, we have found that dyclonine hydrochloride gradually and slowly reaches its maximum activity, e.g. in about 30 minutes, whereas the other anesthetic agents rapidly reach their maximum activity, e.g. within about five minutes or less. However, we have also found that while dyclonine hydrochloride provides long-lasting anesthetic activity, e.g. for about 60 minutes, the rapid-onset anesthetics lose their anesthetic activity much sooner, e.g. within about 20–30 minutes or less.

The present invention now provides an oral anesthetic composition that provides both rapid-onset of anesthetic effect and a long duration of anesthetic effect. In particular, the present invention provides an oral anesthetic composition, comprising an anesthetically effective amount of the compound of formula (I)

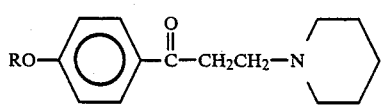

wherein R is alkyl of 2 to 8 carbon atoms or a pharmaceutically acceptable salt thereof and an anesthetically effective amount of a rapid-onset anesthetic selected from the group consisting of benzyl alcohol, phenol, phenolate sodium, hexylresorcinol, menthol, salicyl alcohol and benzocaine in combination with a pharmaceutically acceptable carrier, the composition being in orally administrable form.

The present invention is illustrated in the accompanying drawing, which schematically compares the effects obtained by an oral anesthetic composition of the present invention, comprising anesthetically effective amounts of dyclonine hydrochloride and phenol, with oral compositions comprising an anesthetically effective amount of either dyclonine hydrochloride or phenol.

The data in the FIGURE represent the anesthetic effect of liquid throat sprays containing an anesthetically effective amount of dyclonine hydrochloride or phenol or both dyclonine hydrochloride and phenol. The anesthetic effect of each of the three throat sprays can be determined using the Weinstein Oral Microanesthesiometer (S. Weinstein, Journal of Investigative Dermatology, 69, pages 136–145 (1977)), by spraying a single dose of the candidate anesthetic composition into the oral cavity and taking measurements periodically over time of the oral threshold to air pressure applied to the back of the throat to determine the anesthetic effect. As can be seen from the FIGURE, the throat spray containing an anesthetically effective amount of phenol reached its maximum activity within five minutes, but thereafter it returned to the base line activity (control) after about 20 minutes from the start of the test. In contrast, the throat spray using an anesthetically effective amount of dyclonine hydrochloride gradually reached its maximum anesthetic activity in about 30 minutes, whereafter the anesthetic effect gradually declined. After 60 minutes, the anesthetic effect of the dyclonine hydrochloride throat spray was still above the base line value.

The FIGURE also depicts the effect of the present invention, in which anesthetically effective amounts of dyclonine hydrochloride and phenol are provided in the composition. In the first period (I), the throat spray of the present invention will provide a rapid-onset of activity, usually within about the first five minutes after application, following the pattern of the rapid-onset anesthesic agent. In the second period (II), the anesthetic effect will gradually decline as the rapid-onset anesthetic agent loses its effect while at the same time the anesthetic effect of dyclonine hydrochloride is gradually increasing to its maximum anesthetic activity. In the final period (III), the anesthetic composition of the present invention will provide the anesthetic effect characteristic of dyclonine hydrochloride. As can be seen from the FIGURE, the anesthetic composition of the present invention will provide a rapid onset, long-lasting anesthetic composition having markedly superior properties to both dyclonine hydrochloride and a rapid-onset anesthetic agent, particularly in the first two periods of time (I and II).

The oral anesthetic composition of the present invention comprises an anesthetically effective amount of a compound of formula (I) above wherein R is alkyl of 2 to 8 carbon atoms or a pharmaceutically acceptable salt thereof, preferably dyclonine hydrochloride. See, for example, Bockstahler et al, U.S. Pat. No. 2,771,391; Florestano et al, U.S. Pat. No. 2,868,689 and Lane et al, U.S. Pat. No. 4,139,627. The present invention also includes an anesthetically effective amount of a rapid-onset oral anesthetic agent, such as any of those agents listed in the table above.

Since the anesthetic agents used in the present invention are well known, the anesthetically effective amounts, dosage forms and modes and frequency of administration are known to those skilled in the art. See, e.g. the FDA Monograph referred to above. In this regard, the FDA Monograph is entitled "Tentative Final Monograph", and therefore the anesthetically effective amounts and dosage forms and modes and frequency of administration of the various anesthetic agents, both compound (I), e.g. dyclonine hydrochloride, and the rapid-onset anesthetic agents that are useful in the present invention, will be those amounts and dosage forms recognized by the industry as safe and effective at the time of manufacture and sale of the present invention.

The oral anesthetic composition of the present invention may be in solid dosage form, such as a lozenge, compressed tablet or the like, or in dosage form other than solid, such as a gargle, mouthwash, oral rinse, spray, gel, aerosol or the like. Depending on the dosage form and the anesthetic agent chosen, solid or liquid, aqueous or anhydrous pharmaceutically acceptable carriers may be employed, as is known. For example, it is known that in the absence of a stabilizer benzocaine is generally formulated in an anhydrous carrier to prevent instability thereof. Thus, when benzocaine is used together with compound (I), e.g. dyclonine hydrochloride, in the present invention, an anhydrous pharmaceutically acceptable carrier will be generally employed.

Conventional manufacturing techniques may be employed to manufacture the oral anesthetic composition of the present invention. Thus, the compound and the rapidonset anesthetic agent may be combined in a conventional manner with a desired solid or liquid, anhydrous or aqueous pharmaceutically acceptable carrier, in order to provide a solid or non-solid composition. It is presently preferred to provide the composition as a throat spray, oral rinse or lozenge. Most preferably, the composition of the invention comprises dyclonine hydrochloride and a rapid-onset anesthetic agent as an aqueous oral rinse or throat spray or as a lozenge in a suitable hard candy base.

The present invention is illustrated in terms of its preferred embodiments in the following Examples. In this specification and in the appended claims, all parts and percentages are by weight, unless otherwise stated.

EXAMPLE 1

Lozenges are prepared from the formulation below using conventional hard candy manufacturing equipment. Silicon dioxide is used as a processing aid to facilitate the handling of benzyl alcohol and phenol. Citric acid is used as a stabilizer for the dyclonine hydrochloride in accordance with Lane et al U.S. Pat. No. 4,139,627.

| FORMULATION 1A | | |
|---|---|---|
| | % w/w | Mg per Lozenge |
| Dyclonine HCl USP | 0.13 | 3.2 |
| Benzyl Alcohol | 4.38 | 105.0 |
| Citric Acid USP, Anhydrous | 0.74 | 17.8 |
| Silicon dioxide, Colloidal | 2.50 | 60.1 |
| Oil, Light, Mineral USP | 0.01 | 0.2 |
| Sucrose | 61.25 | 1470.0 |
| Corn Syrup Solids | 29.49 | 707.7 |
| Residual Moisture | 1.50 | 36.0 |
| | 100.00 | 2400.0 |

| FORMULATION 1B | | |
|---|---|---|
| | Formula % w/w | Mg per Lozenge |
| Dyclonine HCl USP | 0.13 | 3.2 |
| Phenol Crystals USP | 2.19 | 52.5 |
| Alcohol USP, Ethanol 190 Proof | 0.15 | 3.7 |
| Citric Acid USP, Anhydrous | 0.74 | 17.8 |
| Silicon dioxide, Colloidal | 0.92 | 22.2 |
| Oil, Light, Mineral USP | 0.01 | 0.1 |
| Sucrose | 63.69 | 1528.5 |
| Corn Syrup Solids | 30.67 | 736.0 |
| Residual Moisture | 1.50 | 36.0 |
| | 100.00 | 2400.0 |

EXAMPLE 2

Liquid anesthetic compositions are prepared from the following formulations and packaged in conventional pump dispensers to provide anesthetic throat sprays.

| FORMULATION 2A | | |
|---|---|---|
| | Formula % w/w | Mg. per Dose (3 ml) |
| Dyclonine HCl USP | 0.11 | 3.7 |
| Benzyl Alcohol | 5.00 | 166.2 |
| Glycerin USP, 99.5% Min. | 36.42 | 1210.6 |
| Alcohol USP, Ethanol 190 Proof | 8.90 | 295.8 |
| Sorbitol USP, 70% Solution | 10.00 | 332.4 |
| Phosphoric Acid NF | 0.10 | 3.3 |
| Sodium Phosphate, Monobasic, Anhydrous | 0.24 | 8.1 |
| Water, High Grade | 39.23 | 1303.9 |
| | 100.00 | 3324.0 |

| FORMULATION 2B | | |
|---|---|---|
| | Formula % w/w | Mg. per Dose (3 ml) |
| Dyclonine HCl USP | 0.11 | 3.7 |
| Phenol USP, Liquid 89% | 1.85 | 61.7 |
| Glycerin USP, 99.5% Min. | 36.42 | 1210.5 |
| Alcohol USP, Ethanol 190 Proof | 8.90 | 295.8 |
| Sorbitol USP, 70% Solution | 10.00 | 332.4 |
| Phosphoric Acid NF | 0.03 | 0.8 |
| Sodium Phosphate, Monobasic, Anhydrous | 0.24 | 8.1 |
| Water, High Grade | 42.45 | 1411.0 |
| | 100.0 | 3324.0 |

We claim:

1. An oral anesthetic composition comprising an anesthetically effective amount of a compound of formula (I)

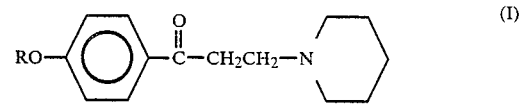

wherein R is alkyl of 2 to 8 carbon atoms or a pharmaceutically acceptable salt thereof and an anesthetically effective amount of a rapid-onset anesthetic selected from the group consisting of hexylresorcinol, and benzocaine in combination with a pharmaceutically acceptable carrier, said carrier being in orally administrable form.

2. The composition according to claim 1, wherein said compound of formula (I) is dyclonine or a pharmaceutically acceptable salt thereof.

3. The composition according to claim 1, wherein said composition is in the form of a liquid .

4. The composition according to claim 1, wherein said composition is in the form of a a lozenge.

5. The composition according to claim 1, wherein said carrier is an orally acceptable solid carrier.

6. The composition according to claim 1, wherein said rapid-onset anesthetic is hexylresorcinol.

7. The composition according to claim 1, wherein said rapid-onset anesthetic is benzocaine.

* * * * *